United States Patent
Sanandajifar et al.

(10) Patent No.: US 10,133,013 B2
(45) Date of Patent: Nov. 20, 2018

(54) APPARATUS AND METHOD OF PROVIDING AN INTERFACE TO AN ELECTRICALLY POWERED INSTRUMENT

(71) Applicant: KARL STORZ Imaging, Inc., Goleta, CA (US)

(72) Inventors: Joseph Sanandajifar, West Hills, CA (US); Mark Belding, Goleta, CA (US); Chris Zimmer, Santa Barbara, CA (US); Carolyn Finney, Goleta, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 76 days.

(21) Appl. No.: 15/161,007

(22) Filed: May 20, 2016

(65) Prior Publication Data

US 2017/0336579 A1 Nov. 23, 2017

(51) Int. Cl.
*G02B 6/42* (2006.01)
*A61B 1/00* (2006.01)
*G02B 6/00* (2006.01)

(52) U.S. Cl.
CPC ........ *G02B 6/4204* (2013.01); *A61B 1/00013* (2013.01); *A61B 1/00029* (2013.01); *A61B 1/00124* (2013.01); *A61B 1/00126* (2013.01); *G02B 6/00* (2013.01); *G02B 6/4278* (2013.01); *G02B 6/4293* (2013.01)

(58) Field of Classification Search
CPC ............................ G02B 6/4204; G02B 6/4278
USPC .......................................................... 385/93
See application file for complete search history.

(56) References Cited

U.S. PATENT DOCUMENTS

| | | |
|---|---|---|
| 7,354,205 B2 | 4/2008 | Sakata |
| 7,914,443 B2 | 3/2011 | Uchimura |
| 8,419,622 B2 | 4/2013 | Shimotsu |
| 8,465,330 B2 | 6/2013 | Miyagi |
| 8,556,521 B2 | 10/2013 | Everett |
| 8,714,836 B2 | 5/2014 | Daikuhara |

(Continued)

FOREIGN PATENT DOCUMENTS

| | | |
|---|---|---|
| EP | 1721568 A1 | 11/2006 |
| JP | 2006051162 A | 2/2006 |

(Continued)

*Primary Examiner* — Jerry Blevins
(74) *Attorney, Agent, or Firm* — Michael Loi; David Villalpando (57) ABSTRACT

An interface device includes first and second connectors adapted to be joined together in an operating position. One or more first optical data conduits extend through the first connector, with each first optical data conduit terminating at a respective first optical conduit end which is operatively aligned with a respective first optical lens. One or more second optical data conduits extend through the second connector, with each second optical data conduit terminating at a respective second optical conduit end which is operatively aligned with a respective second optical lens. Each respective second optical data conduit and respective second optical lens are aligned for optical coupling across a coupling region with one of the first optical conduits and respective first optical lens when the first connector and second connector are joined in the operating position. The interface also includes a wireless or contact-type electrical power transfer arrangement.

14 Claims, 8 Drawing Sheets

(56) References Cited

U.S. PATENT DOCUMENTS

| | | | |
|---|---|---|---|
| 9,195,008 B2 | 11/2015 | Farnan | |
| 2007/0060789 A1* | 3/2007 | Uchimura | A61B 1/00016 600/110 |
| 2007/0282165 A1 | 12/2007 | Hopkins | |
| 2008/0208006 A1 | 8/2008 | Farr | |
| 2008/0225134 A1 | 9/2008 | Amling | |
| 2010/0027943 A1 | 2/2010 | Armani | |
| 2014/0184771 A1 | 7/2014 | Mazzetti | |
| 2015/0141751 A1 | 5/2015 | Finkman | |
| 2015/0250378 A1 | 9/2015 | Tomatsu | |
| 2016/0089000 A1 | 3/2016 | Hara | |
| 2017/0006264 A1 | 1/2017 | Tomatsu | |

FOREIGN PATENT DOCUMENTS

| | | |
|---|---|---|
| JP | 2006181021 A | 7/2006 |
| WO | 2014106059 | 7/2014 |
| WO | 2015107852 | 7/2015 |

* cited by examiner

APPARATUS AND METHOD OF PROVIDING AN INTERFACE TO AN ELECTRICALLY POWERED INSTRUMENT

TECHNICAL FIELD OF THE INVENTION

The invention relates to electrical power and data interfaces with observation instruments, including optical instruments such as endoscopic devices. More particularly, the invention relates to connectors which are used to provide an interface between an electrically operated instrument and control or related equipment for the instrument. The invention also relates to methods for providing such an interface.

BACKGROUND OF THE INVENTION

Observation instruments, including optical instruments such as endoscopes, borescopes, and exoscopes may include an electronic imaging device located, for example, at the distal end of an elongated shaft or in a camera head which is connected to an elongated shaft. Whether positioned at the distal end of the endoscope shaft or in the camera head, the electronic imaging device may be one or more charge coupled devices (CCDs) or CMOS imaging devices together with other electronic components. Other electronic devices such as LED or other light sources may be included in the instrument. The camera head (or an instrument body or handle in the case of some observation instruments) is typically connected via a suitable cable to a camera control unit, commonly referred to as a "CCU." The cable provides paths for carrying electrical power to the camera head and data signals to and from the camera head. In particular, image data captured by the imaging device is transmitted over the cable to the CCU for processing and ultimately for display on monitors which are connected directly to the CCU or to an intermediate monitor driving device. Control signals and power for operating the electronic components in the instrument may be transmitted over the cable from the CCU to the scope and/or camera head.

It is known in the art to transmit data signals from an endoscope to a CCU in the form of optical signals rather than electrical signals. U.S. Patent Application Publication 2015/0250378, for example, uses a cable between a camera head and CCU which includes optical fibers for carrying optical data signals from the camera head to the CCU. The camera head in this example includes circuitry for converting the captured image data from the electronic data signals generated by the imaging device to optical data signals which are then inserted into the optical fibers of the cable. U.S. Patent Application Publication 2015/0250378 also discloses that the cable from the camera head to CCU may include electrical signal paths in addition to the optical signal paths.

U.S. Patent Application Publication 2008/0225134 shows another endoscopic system having a cable between the CCU and camera head which includes both electrical signal paths and an optical path. In this case, the optical path is used to provide illumination light to the endoscope.

Medical devices such as endoscopes require an electrical isolation barrier between the CCU and camera head/endoscope. This electrical isolation barrier is required to ensure that an inappropriate electrical signal is not inadvertently applied to the endoscope and thus to the patient in which the endoscope is used. Where a cable running between the CCU and endoscope includes electrical signal paths, such as in both of the above-mentioned U.S. patent application publications, it has been necessary for the electrical isolation barrier to be included in the circuitry of the CCU. This requirement of the electrical isolation barrier in the CCU greatly complicates the circuitry of the device.

SUMMARY OF THE INVENTION

It is an object of the invention to provide and interface to an electrically powered instrument in which the interface is robust and supports high data transfer rates, particularly in the direction from the instrument to control equipment for the instrument. Another object of the invention is to provide such an interface which includes an electrical isolation barrier.

An interface device according to one aspect of the present invention includes a first connector and a second connector adapted to be joined together in an operating position. One or more first optical data conduits such as optical fibers extend through the first connector, with each first optical data conduit terminating at a respective first optical conduit end which is operatively aligned with a respective first optical lens. One or more second optical data conduits (which may similarly comprise optical fibers) extend through the second connector, with each second optical data conduit terminating at a respective second optical conduit end which is operatively aligned with a respective second optical lens. When the first connector and second connector are joined in the operating position, each respective second optical data conduit and respective second optical lens are aligned for optical coupling across a coupling region with one of the first optical conduits and respective first optical lens. This arrangement of optical data conduits and optical lenses produces an expanded beam optical data communication path across the two connectors for each pair of aligned first and second optical conduits.

As used in the preceding paragraph and elsewhere in this disclosure and following claims, the designation "operatively aligned" with reference to an optical fiber end and an optical lens means that the fiber end is aligned so that the light signal exiting the fiber end is incident on the lens surface so that the lens provides the desired optical function. The function of the optical lenses will be described further below in connection with the representative embodiments. The designation "optical coupling" in the present disclosure and accompanying claims means an arrangement in which light exiting a fiber end passes through the corresponding optical lenses and is directed into the end of the corresponding optical fiber.

In addition to the optical elements according to this first aspect of the invention, the interface also includes an electrical power transfer arrangement. This arrangement includes a first electrical power transfer element mounted on the first connector and a second electrical power transfer element mounted on the second connector. These electrical power transfer elements are located in a power transfer orientation with respect to each other when the first connector and second connector are joined in the operating position, and this facilitates the transfer of electrical power from one of the connectors to the other.

The expanded beam optical data communication arrangement together with the electrical power transfer arrangement has the advantage that very high data transfer rates are possible across the interface, while electrical power for electronic components may also be transferred across the interface. High data transfer rates are particularly advantageous where the interface is used in medical instrument systems such as video endoscope systems in which a high-resolution image is captured with electronic components at the instrument, and then the voluminous image data is transferred to a control system for processing. The expanded beam optical communication arrangement accommodates the high data rates which may be required while the power transfer arrangement accommodates the transfer of electrical power to the imaging and optical signal generation elements required for image collection and optical data communication.

Furthermore, in some embodiments of the interface, the electrical power transfer elements may be configured so that the electrical power is transferred inductively across the elements. Thus all electrical circuits associated with the first connector may be electrically isolated from all electrical circuits associated with the second connector. With the data all communicated along optical communication paths across the interface, and with the electrical circuits electrically isolated, the interface forms an electrical isolation barrier. The interface may be placed at any one of a number of alternative locations in a medical device system such as an endoscopic system to eliminate the need for a complicated electrical isolation barrier in the system control equipment.

Another aspect of the invention provides a single connector similar to one of the connectors described above. Such a connector has particular application in making a connection with a complementary connector to provide a detachable interface between an electrically powered instrument and a control system for the instrument. A connector according to this second aspect of the invention includes a connector body and an optical data conduit extending through the connector body and terminating at a conduit end within the connector body. An optical lens is included in the connector body and is operatively aligned with the conduit end. An electrical power transfer element is also mounted within the connector body.

A connector according to either of the above aspects of the present invention may include a cable connected to the connector body. The cable may include continuations of the optical data conduits of the connector and also electrical conductors for carrying the desired electrical power signal to or from the connector. Of course, where electrical isolation is provided across a connection made by the connectors, all electrical circuits included in the connector are electrically isolated within the connector body aside from electrical continuity to the power conductor arrangement within the cable.

Another aspect of the invention includes a method of providing an interface between an electrically powered instrument and a control system for the instrument. A method according to this additional aspect of the invention includes placing a first connector in an operating position with respect to a second connector and directing optical data along an optical path defined through the first and second connectors in the operating position. This optical path includes a first optical conduit extending through the first connector, second optical conduit extending through the second connector, and a coupling region interposed between the first optical conduit and the second optical conduit. A method according to this additional aspect of the invention further includes expanding an area of an optical signal (the signal carrying the optical data) at a first side of the coupling region and reducing the area of the optical signal at a second side of the coupling region. Additionally, electrical power is transferred from a first power transfer element included with the first connector to a second power transfer element included with the second connector.

In one implementation of an interface according to any of the foregoing aspects of the invention, the first connector defines a receptacle. In these implementations when the connectors are in the operating position at least a portion of the second connector is received within the receptacle defined by the first connector. Also, where the interface is employed in an endoscopic system, the connector defining the receptacle may advantageously be contained within a housing for a camera control unit of the endoscopic system.

As noted above, embodiments of the interface may employ an inductive coupling between the power transfer elements in order to maintain electrical isolation between the two complementary connectors. Any suitable inductive coupling arrangement may be employed according to the invention. In one implementation, the first electrical power transfer element comprises a first planar spiral coil and the second electrical power transfer element comprises a second planar spiral coil. In these planar coil implementations, the first planar spiral coil may be aligned parallel to a first side of the first connector and the second planar spiral coil may be aligned parallel to a first side of the second connector. The two planar spiral coils align with each other sufficiently when the connectors are in the operating position to provide inductive coupling between the coils. Alternatively to the planar coil implementations, the electrical power transfer elements may comprise helical coils. In particular, the first electrical power transfer element may comprise a first helical coil and the second electrical power transfer element may comprise a second helical coil adapted to align with the first helical coil and reside within an area defined by the first helical coil when the first connector and the second connector are joined in the operating position.

In any of the different aspects of the present invention, a suitable transparent protective material may be mounted on the respective connector to protect the optical lens or lenses. In particular, the transparent protective layer may be mounted on the respective connector in position to reside between each optical lens of that connector and the opposite connector when the connectors are in the operating position.

In any of the different aspects of the present invention, the electrically powered instrument may be an observation instrument. Such an observation instrument might be an optical instrument such as a video camera, endoscope, exoscope, or borescope.

These and other advantages and features of the invention will be apparent from the following description of representative embodiments, considered along with the accompanying drawings.

DESCRIPTION OF REPRESENTATIVE EMBODIMENTS

The present invention is disclosed below in the context of an endoscopic system. Embodiments also include apparatus and methods for other electrically powered instruments. Thus, optical instruments (e.g., video cameras, endoscopes, exoscopes, borescopes) employing high-resolution imaging (e.g., a 4K resolution design) is an illustrative, but non-limiting example embodiment. More generally, an interface or connector within the scope of the following claims may have application in connection with any observation instrument.

Figure 1:
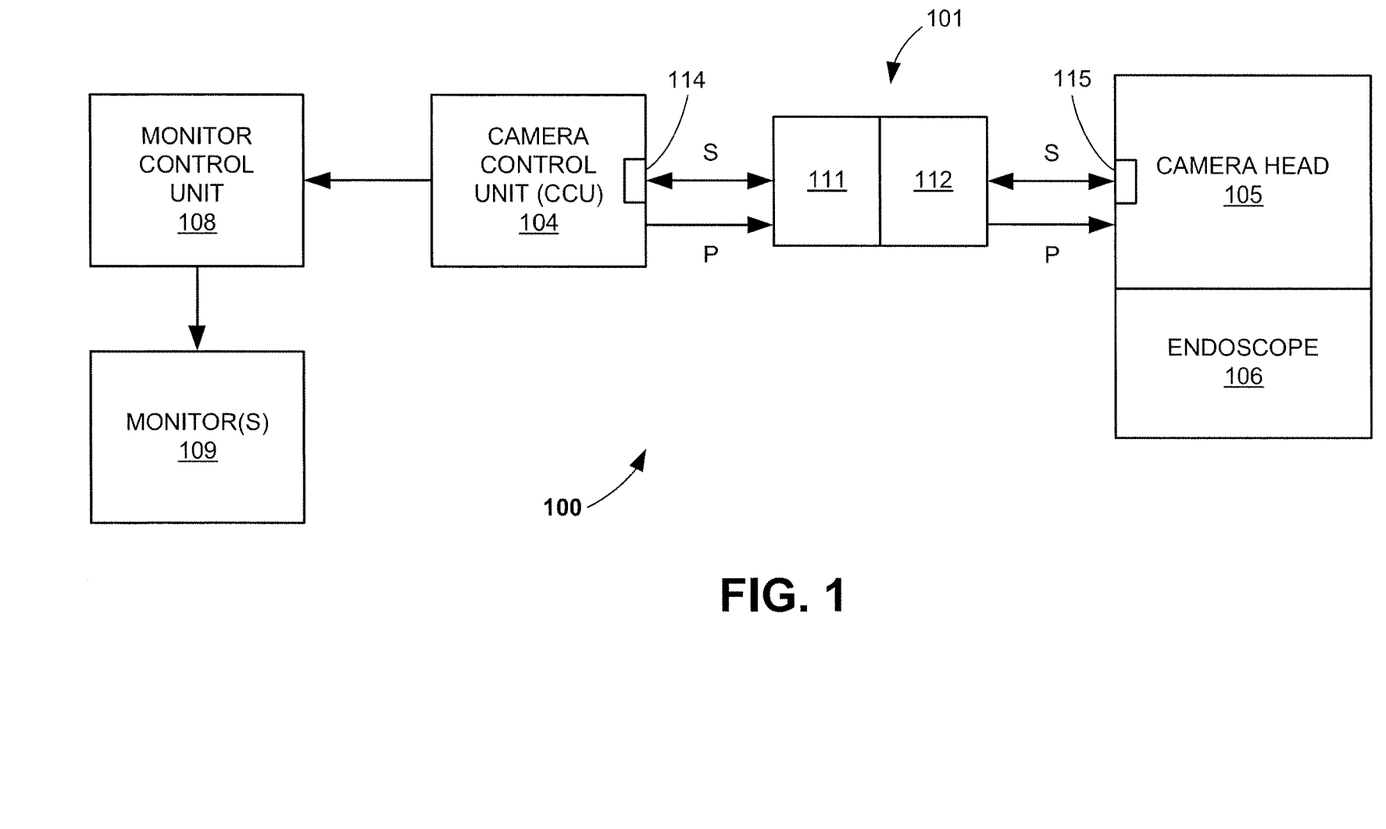
FIG. 1 is a block diagram showing an endoscopic system incorporating an interface device according to an aspect of the present invention.

FIG. 1 shows an endoscopic system 100 employing an interface device 101 according to the present invention. System 100 includes a camera control unit ("CCU") 104, a camera head 105, and an endoscope 106. CCU 104 is connected to send a signal to a monitor control unit 108 connected to monitors 109 for displaying images from camera head 105 or endoscope 106.

Interface device 101 is interposed between CCU 104 and camera head 105 and functions as a detachable link for data communication and power transfer between the CCU and camera head. Both the data communication and power transfer functions are preferably provided across interface device 101 while the device also maintains an electrical isolation barrier to camera head 105 and endoscope 106. Data is communicated in the form of optical data signals S in FIG. 1, both from camera head 105 and/or endoscope 106 to CCU 104 and also preferably in the opposite direction from the CCU to the camera head and/or endoscope. Electrical power (P in FIG. 1) is transferred only in the direction from CCU 104 to camera head 105 and/or endoscope 106. The data transmission rates possible via optical data transmission in the direction from the camera head 105 to CCU 104 is particularly advantageous for transmitting the large amounts of image data that may be collected by an imaging device or multiple imaging devices (not shown) associated with endoscope 106 or camera head 105. Data which may be transmitted from CCU 104 to camera head 105 and/or endoscope 106 may comprise control instructions and operational instructions and data, which may typically be of lesser volume as compared to the image data transmitted in the opposite direction.

Interface device 101 includes a first connector 111 and a second connector 112 which may be connected in an operating position to facilitate the desired data communication and power transfer. This operating position is schematically indicated in FIG. 1 and will be described in further detail below with reference particularly to FIGS. 2 and 9. The two connectors 111 and 112 may be readily separated to detach camera head 105 and endoscope 106 from CCU 104 and then reconnected in the operating position as desired. For example, connector 112 may be detached from connector 111 in preparation for sterilizing camera head 105 and/or endoscope 106. Once the sterilization or other process or activity requiring detachment is complete, connectors 111 and 112 may be readily connected back together again in the operating position to again facilitate data communication and power transfer between CCU 104 and camera head 105/endoscope 106.

The position of interface device 101 shown in FIG. 1 between CCU 104 and camera head 105 is intended to indicate that the device may be interposed at any position between those two devices. One embodiment that will be described further below in connection with FIGS. 2 and 6-9 incorporates first connector 111 in a housing for CCU 104. In this embodiment, first connector 111 may be formed as a receptacle in a housing for CCU 104 and adapted to receive second connector 112 in the operating position. Second connector 112 in this embodiment is connected to a suitable cable having optical conduits such as optical fibers for carrying the optical signals and suitable conductors for conducting electrical power to camera head 105. Such a cable will be described below in connection with FIG. 5. However it should be borne in mind that the invention is not limited to this arrangement in which one of the connectors is incorporated in the CCU or one of the other devices in the system.

Before moving on to describe further details of interface device 101, it should be noted that both CCU 104 and camera head 105 include components for supporting the interface. In particular, CCU 104 includes a signal conversion unit 114 to convert incoming optical signals from the direction of camera head 105 to electrical signals for further processing and to convert electrical signals generated at the CCU to optical signals for transmission to the camera head and/or endoscope 106. Similarly camera head 105 includes a signal conversion unit 115 for converting image data and other signals to optical signals for transmission to CCU 104 and for converting incoming optical signals from the CCU to electrical signals for use in the camera head or endoscope 106.

Figure 2:
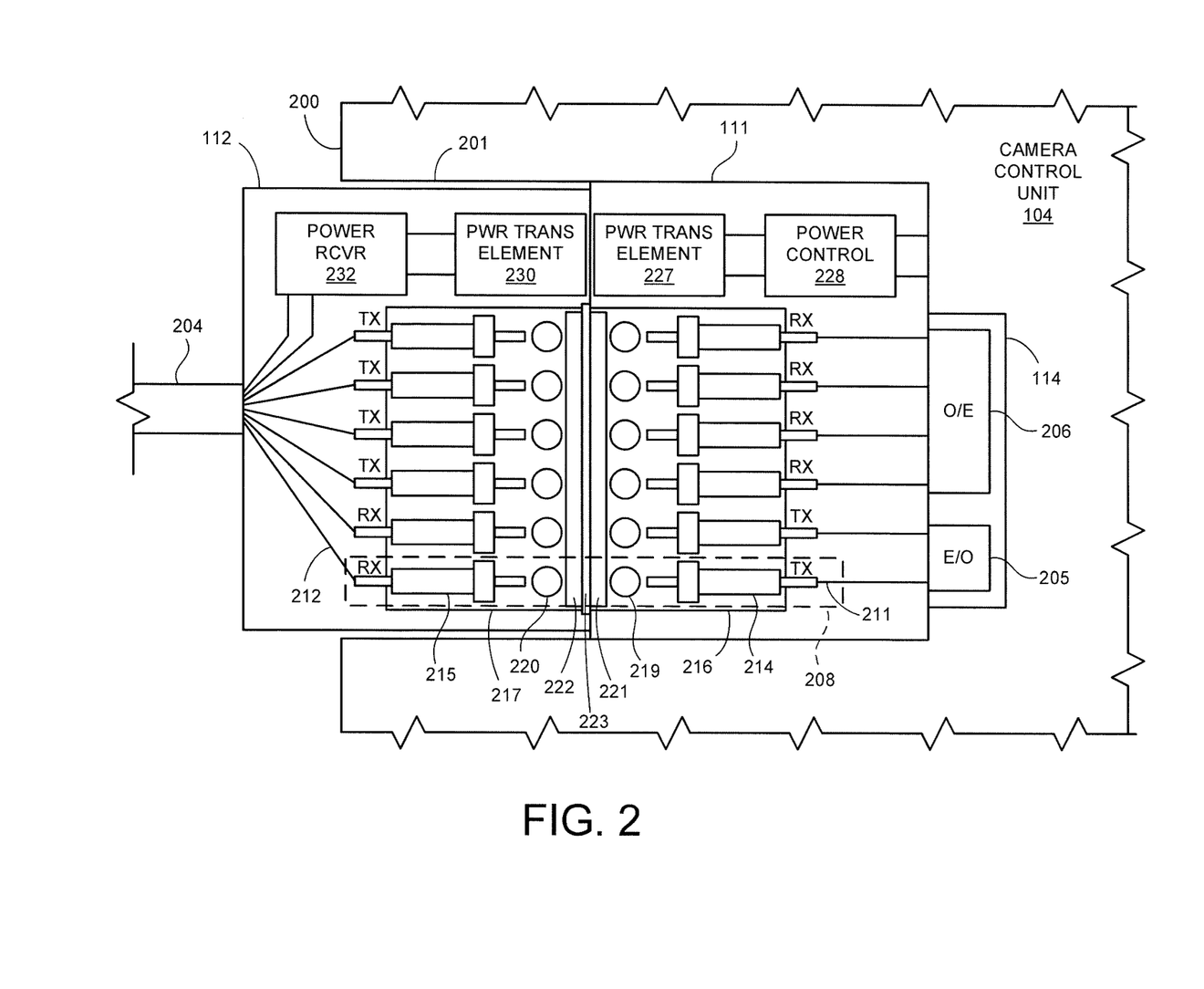
FIG. 2 is a schematic diagram of the interface device shown in FIG. 1.

FIG. 2 shows an embodiment of interface 101 with first connector 111 incorporated in a housing 200 for CCU 104. First connector 111 defines a receptacle 201 in CCU housing 200 which is adapted to receive second connector 112 in the operating position shown in the figure. Second connector 112 in this illustrated embodiment is connected to a cable 204 which includes elements for carrying the optical signals and electrical signals to camera head 105 shown in FIG. 1. Further details of a suitable cable will be described below with reference to FIG. 5.

In order to support the optical data signal communications through interface 101, CCU 104 includes signal conversion unit 114. Signal conversion unit 114 includes an electro-optical converter 205 for converting electrical signals from CCU 104 to optical signals for transmission in the direction to camera head 105. Signal conversion unit 114 also includes an opto-electrical converter 206 for converting optical signals received from camera head 105 and/or endoscope 106 to electrical signals for processing in other elements (not shown) of CCU 104. The electro-optical converter 205 and opto-electrical converter 206 included in signal conversion unit 114 are well known in the art. Thus these signal conversion elements will be described herein only generally so as not to obscure the present invention in unnecessary detail.

The embodiment shown in FIG. 2 includes six different optical signal paths. A portion of one such optical signal path is shown within dashed box 208 in FIG. 2. Each optical signal path is defined in part by a first optical fiber 211 associated with first connector 111 and a second optical fiber 212 associated with second connector 112. First optical fiber 211 terminates in connector 111 in a suitable ferrule 214, while second optical fiber 212 terminates in connector 112 in a corresponding ferrule 215. Each ferrule 214 in connector 111 is mounted in an alignment block 216 mounted in that connector. Similarly, each ferrule 215 in connector 112 is mounted in an alignment block 217 mounted in that connector. Each alignment block 216 and 217 is positioned to align with the opposite alignment block when connectors 111 and 112 are in the illustrated operating position so as to align the terminating end of each optical fiber 211 with the terminating end of the corresponding fiber 212 in the respective optical signal path.

Each optical signal path in this illustrated form of the invention also includes an expanded beam coupling arrangement for coupling the optical signal carried through one fiber 211 or 212 to the optical fiber included with the opposite connector. The expanded beam arrangement for a given optical signal path includes an optical lens 219 aligned with the terminating end of optical fiber 211, and an optical lens 220 aligned with the terminating end of optical fiber 212. Optical lens 219 for an incoming optical signal from fiber 211 in the lowermost optical signal path shown in dashed box 208 in FIG. 2 is operable to expand and collimate the incoming optical signal to distribute the optical power of the signal over a larger area (larger than the fiber) within the coupling region defined between the two lenses 219 and 220. On the opposite side of the interface along the lowermost signal path, optical lens 220 serves to focus the expanded beam back down to the area defined by the terminating end of optical fiber 212 in which the signal is to be inserted. Thus the arrangement of operatively aligned fiber 211 and optical lens 219, and corresponding operatively aligned fiber 212 and optical lens 220 along a given optical path provides an optical coupling that couples a light signal exiting one of the fiber ends into the end of the corresponding fiber.

It should be noted here that although the representative embodiment shown in FIG. 2 and embodiments described below in connection with FIGS. 6-9 show ball lenses for lenses 219 and 220, the present invention is not limited to embodiments using ball lenses. Other embodiments may employ GRIN lenses, aspherical lenses, or drum lenses with spherical surfaces, for example. Also, although the various elements of an optical signal path are labeled in FIG. 2 only for the path in dashed box 208. The reference signs for the path in dashed box 208 apply to the corresponding elements of the other five optical signal paths.

First connector 111 and second connector 112 each includes a suitable protective transparent cover extending transverse to each signal path. The protective cover for first connector 111 is shown at 221 in FIG. 2, while the protective cover for second connector 112 is shown at 222. Protective covers 221 and 222 may comprise Sapphire or any other suitable material and forms an exterior surface of the respective connector covering the adjacent optical lens. This arrangement protects optical lenses 219 and 220 from damage when connectors 111 and 112 are not connected in the operating position shown in FIG. 2.

In the embodiment of the invention shown in FIG. 2, first and second connectors 111 and 112, respectively, are configured to leave an air gap 223 between covers 221 and 222 when the connectors are connected together in the operating position. Each optical signal path, such as the path shown in dashed box 208, includes a portion traversing this air gap 223. Air gap 223 is used to prevent contact between the covers 221 and 222, and may be very narrow, on the order of 1 mm or less. It will be appreciated that other embodiments of the connectors 111 and 112 may be configured so that there is essentially no air gap between covers 221 and 222. Rather, the outer surfaces of covers 221 and 222 may abut each other when connectors 111 and 112 are connected together in the operating position.

The example provided in FIG. 2 shows four optical paths (the upper four in the figure) dedicated for optical transmissions in the direction from camera head 105 to CCU 104. These optical transmissions (in the illustrated use in an endoscopic system 100 in FIG. 1) will include image data which may include a very large volume of data depending upon the resolution of the imaging device associated with camera head 105 or endoscope 106 and on other factors. In this example, two optical paths (the lower two in FIG. 2) are dedicated for the transmission of optically encoded data in the direction from CCU 104 to camera head 105. This data may include instructions and control signals for camera head 105 and/or endoscope 106. It should be appreciated that the invention is not limited to any particular number of optical paths or any particular optical encoding technique. Although FIG. 2 suggests that each optical signal path accommodates only unidirectional data transmission, other embodiments may include bidirectional transmission over each optical path. Also, various optical signal encoding techniques may be employed to further increase the rate at which data may be transmitted through interface 101. For example wave division multiplexing techniques or other multiplexing techniques may be used to transmit multiple different data streams contained in a single multiplexed signal across a given optical signal path. Of course the receiving and transmitting elements in CCU 104 and camera head 105 must support the respective encoding and transmission technique employed across the optical signal paths. For example, signal multiplexing techniques employ a multiplexer at the transmission side and a demultiplexer at the receiving side.

Interface 101 shown in FIG. 2 also includes an arrangement for wirelessly transferring power from first connector 111 on the CCU side of the interface to second connector 112 on the camera head side of the interface. This electrical power supplied to camera head 105 and/or endoscope 106 is necessary for operating electronic elements included in the camera head and endoscope. For example, the electrical power may be used to operate an imaging device and related electronic components in camera head 105 or endoscope 106, opto-electrical and electro-optical converters associated with the camera head, and illumination elements (not shown in the figures) associated with the camera head and/or endoscope. The wireless power transfer arrangement includes a first power transfer element 227 included with first connector 111, and a power control circuit 228 connected to the first power transfer element. A second power transfer element 230 is included with second connector 112 together with a power receiver or conditioner 232. When the two connectors 111 and 112 are connected in the operating position indicated in FIG. 2, the two power transfer elements 227 and 230 are in a power transfer orientation with respect to each other, which, in this embodiment comprises an orientation in which the power transfer elements are inductively coupled. Power control circuit 228 is operable to supply a suitable driving signal to cause a variable current flow in first power transfer element 227 and consequent electromagnetic field around the first power transfer element. This field produced around first power transfer element 227 induces a current in second power transfer element 230. The induced current is conditioned by power receiver/conditioner circuit 232 to provide a suitable power signal for transmission to the camera head over electrical conductors included in cable 204. For example, power receiver/conditioner circuit 232 may comprise a suitable rectifying circuit for converting the signal induced in second power transfer element 230 to a DC voltage signal suitable for use by electronic components included in camera head 105 and endoscope 106 (shown in FIG. 1).

This preferred arrangement of wireless power transfer between connectors 111 and 112 results in complete electrical isolation between electrical circuits associated with the first connector and electrical circuits associated with the second connector. Thus interface 101 itself made up of connectors 111 and 112 provides the required electrical isolation barrier between CCU 104 and camera head 105/endoscope 106. This electrical isolation barrier included in interface 101 obviates the need for an electrical isolation barrier in the circuitry of CCU 104, which is typically complicated and serves as a constraint on CCU design.

It should be appreciated that although the wireless power transfer arrangement across connectors 111 and 112 represents a preferred form of the present invention, alternative embodiments may include a contact-type power transfer arrangement which relies on electrical contacts in the connectors. In this alternative arrangement the first power transfer element comprises a pair of electrical contacts (positive and negative) associated with one connector while the second power transfer element comprises a corresponding pair of electrical contacts associated with the other connector. The like polarity contacts in these two pairs of electrical contacts would simply make contact with each other when connectors 111 and 112 are connected in the operating position. This contacting position represents the power transfer orientation in this contact-type embodiment. Of course, the contact-type embodiments do not provide the electrical isolation provided by the embodiment shown in FIG. 2. Thus a system such as system 100 in FIG. 1 employing a data and power interface having a contact-type power transfer arrangement would have to provide an electrical isolation barrier outside of the interface.

Figure 3:
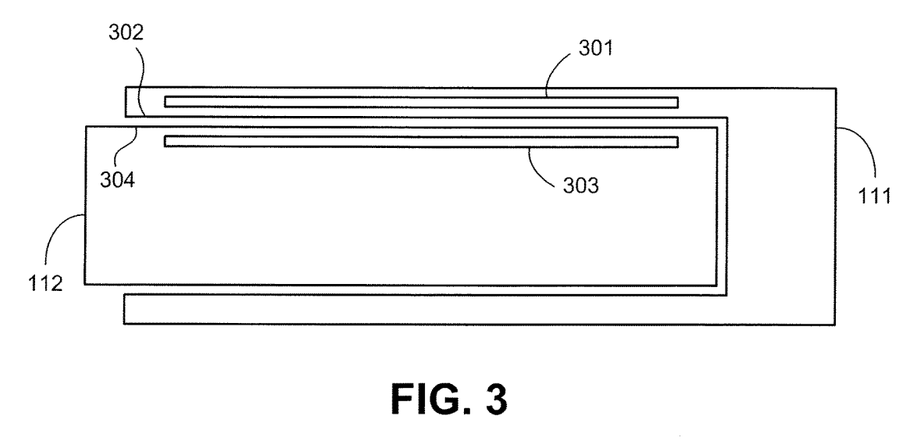
FIG. 3 is a schematic representation showing a power transfer element arrangement according to one embodiment of the invention.
Figure 4:
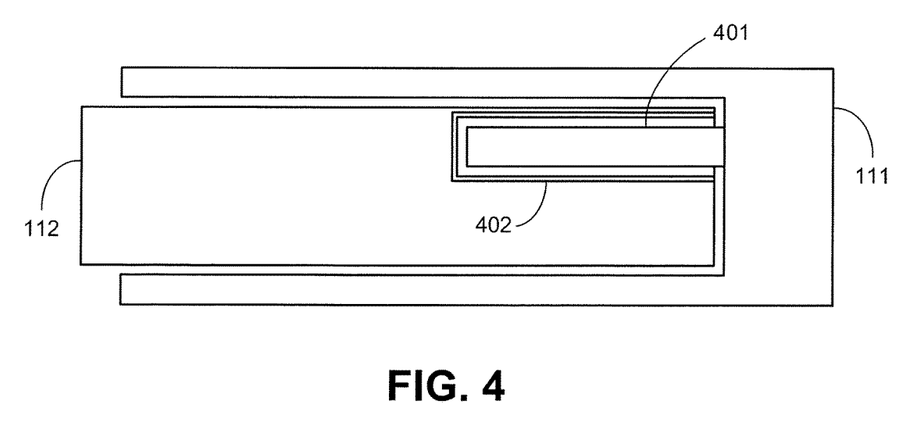
FIG. 4 is a schematic representation showing a power transfer element arrangement according to another embodiment of the invention.

FIGS. 3 and 4 show alternative arrangements for first and second power transfer elements, 227 and 230, respectively, shown in FIG. 2. The high-level schematic diagram of FIG. 3 shows that the first and second power transfer elements may each comprise a suitable planar spiral coil. In particular, a first planar spiral coil 301 comprises the power transfer element associated with first connector 111, and is aligned with its plane parallel to a first side 302 of that connector. This side 302 forms an inner surface of the receptacle defined by first connector 111 in this example. A second planar spiral coil 303 comprising the power transfer element associated with second connector 112 is mounted parallel to a side surface 304 of that connector. When first connector 111 and second connector 112 are placed in the operating position indicated in FIG. 3, the spiral coil 301 comprising the first power transfer element aligns with the spiral coil 303 comprising the second power transfer element so that the two coils are inductively coupled.

The high-level schematic diagram in FIG. 4 shows an alternative arrangement in which a helical coil 401 comprises the power transfer element associated with the first connector 111. This helical coil 401 protrudes from first connector 111 into the area defined by the receptacle of the first connector. A second helical coil 402 comprises the power transfer element associated with second connector 112. Helical coil 402 in this embodiment has a diameter large enough to receive helical coil 401. When first connector 111 and second connector 112 are placed in the operating position with the second connector received in the receptacle defined by the first connector, helical coil 401 comprising the first power transfer element aligns with and extends into helical coil 402 comprising the second power transfer element so that the two coils are inductively coupled to facilitate the desired power transfer. Of course other arrangements within the scope of the present invention may reverse the helical coils so that a helical coil on connector 112 extends into the area defined by a larger diameter helical coil on connector 111.

Figure 5:
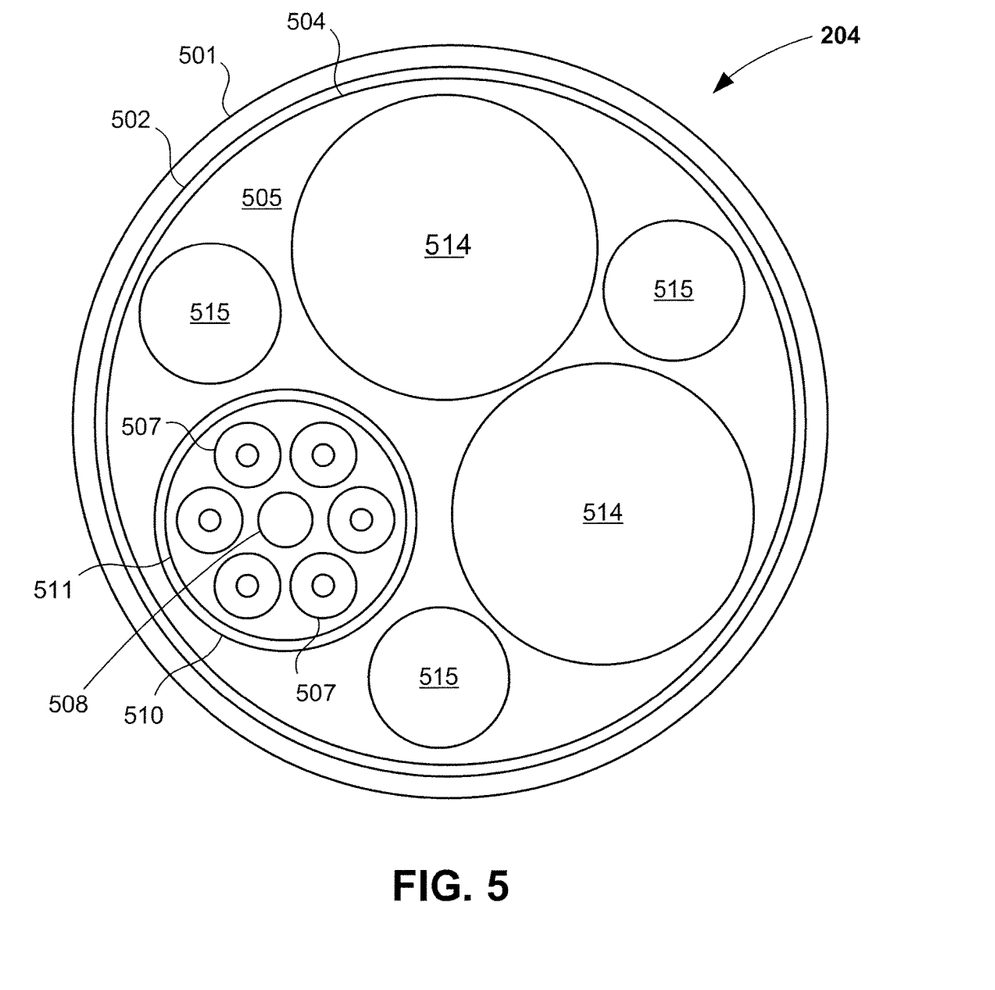
FIG. 5 is a schematic representation of a cross-section of a cable that may be employed with the interface device shown in FIG. 2.

The schematic representation of FIG. 5 shows a cable structure which may be employed for cable 204 shown in FIG. 2. In this example, cable 204 includes a cover material 501 lined inside by a moisture protection layer 502 and an EMF shielding layer 504. These three layers 501, 502, and 504 define and interior area 505 for optical fibers, electrical conductors, and reinforcing elements as desired. In particular, interior area 505 provides room for six optical fibers 507, which, together with a filler or reinforcing element 508 are grouped together in a mono coil 510 lined with a suitable protective layer 511. Area 505 also provides room for two conductors 514 (separate power and ground conductors) which may comprise sheathed AWG 26 copper wire for example. The example of FIG. 5 also shows three strands of filler/reinforcement 515. It will be appreciated that optical fibers 507 shown in FIG. 5 comprise the continuation of fibers 212 which terminate in second connector 112 in FIG. 2. Conductors 514 terminate in second connector 112 shown in FIG. 2 at power receiver/conditioner 232.

This cable arrangement shown in FIG. 5 has the advantage that the bundle of optical fibers may be readily changed as desired by simply pulling the fiber 507 and filler/reinforcement strand 508, and replacing that bundle with another bundle having more or fewer fibers. Cable 204 shown in FIG. 5 may also be modified by using the conductive mono coil 510 and the EMF shielding 504 to replace the two copper conductors 514. This allows the cable to have a smaller diameter, or allows the area taken up by conductors 514 to be used for additional optical fibers, preferably run in one or more additional mono coils. In any event, the combination of optical fiber transmission elements together with the electrical conductors allows the cable to support the optical data transmission and electrical power transfer facilitated by interface 101.

Figure 6:
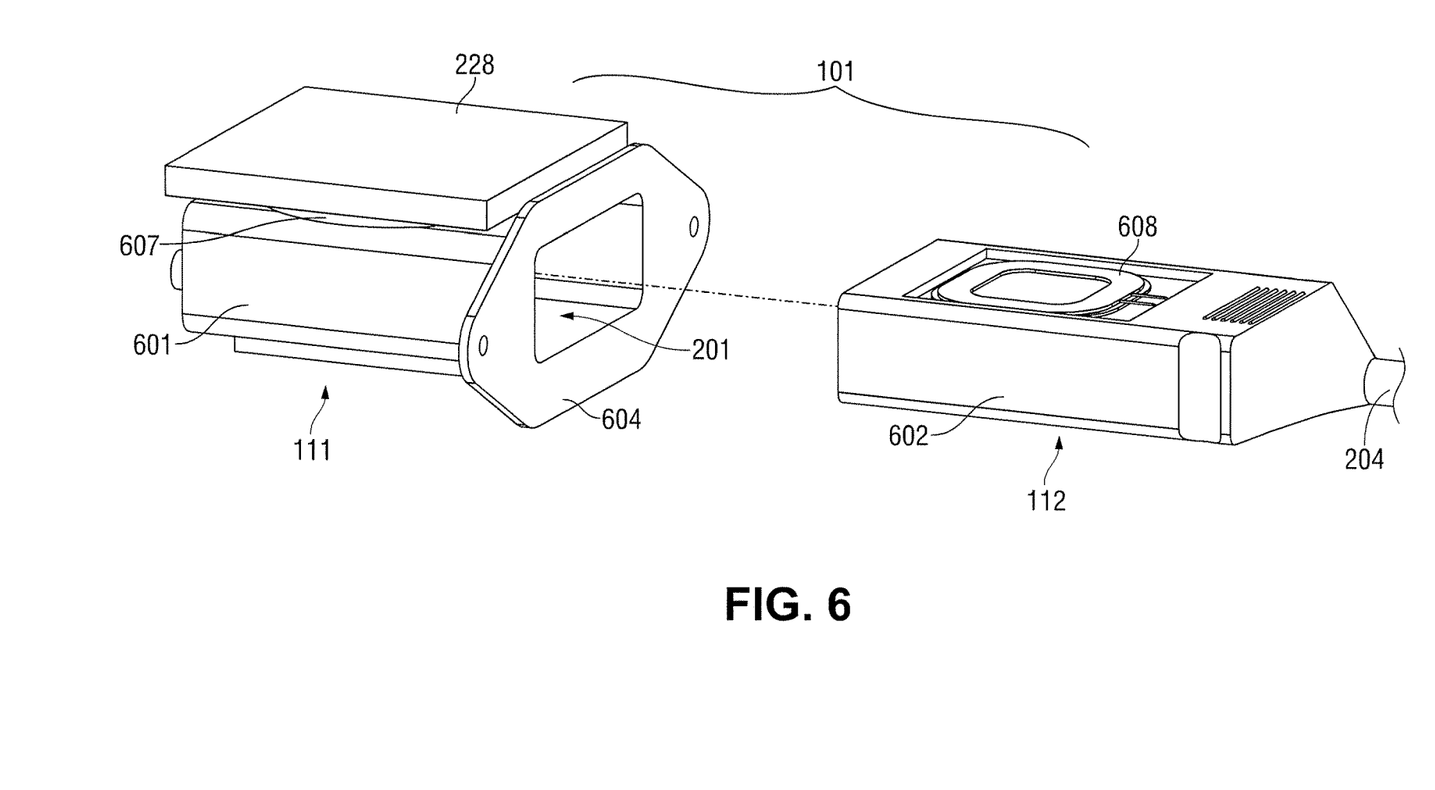
FIG. 6 is a view in perspective showing a pair of connectors making up an interface device according to an embodiment of the invention.

FIGS. 6 through 9 show an example of an interface device 101 in which first connector 111 is adapted to be incorporated with the housing of another component such as CCU 104 shown in FIG. 1. As shown in FIG. 6, first connector 111 includes a housing 601 while second connector 112 includes a housing 602. Housings 601 and 602 each provide an enclosure for components of the respective connector. Housing 601 also includes a flange 604 by which first connector 111 may be secured to a component such as CCU 104 in FIG. 1. Housing 601 also defines a receptacle 201 in which housing 602 for connector 112 can be inserted to place the two connectors in the operating position. Second connector 112 is connected to cable 204 which extends to a camera head or endoscope such as those described above.

Figure 7:
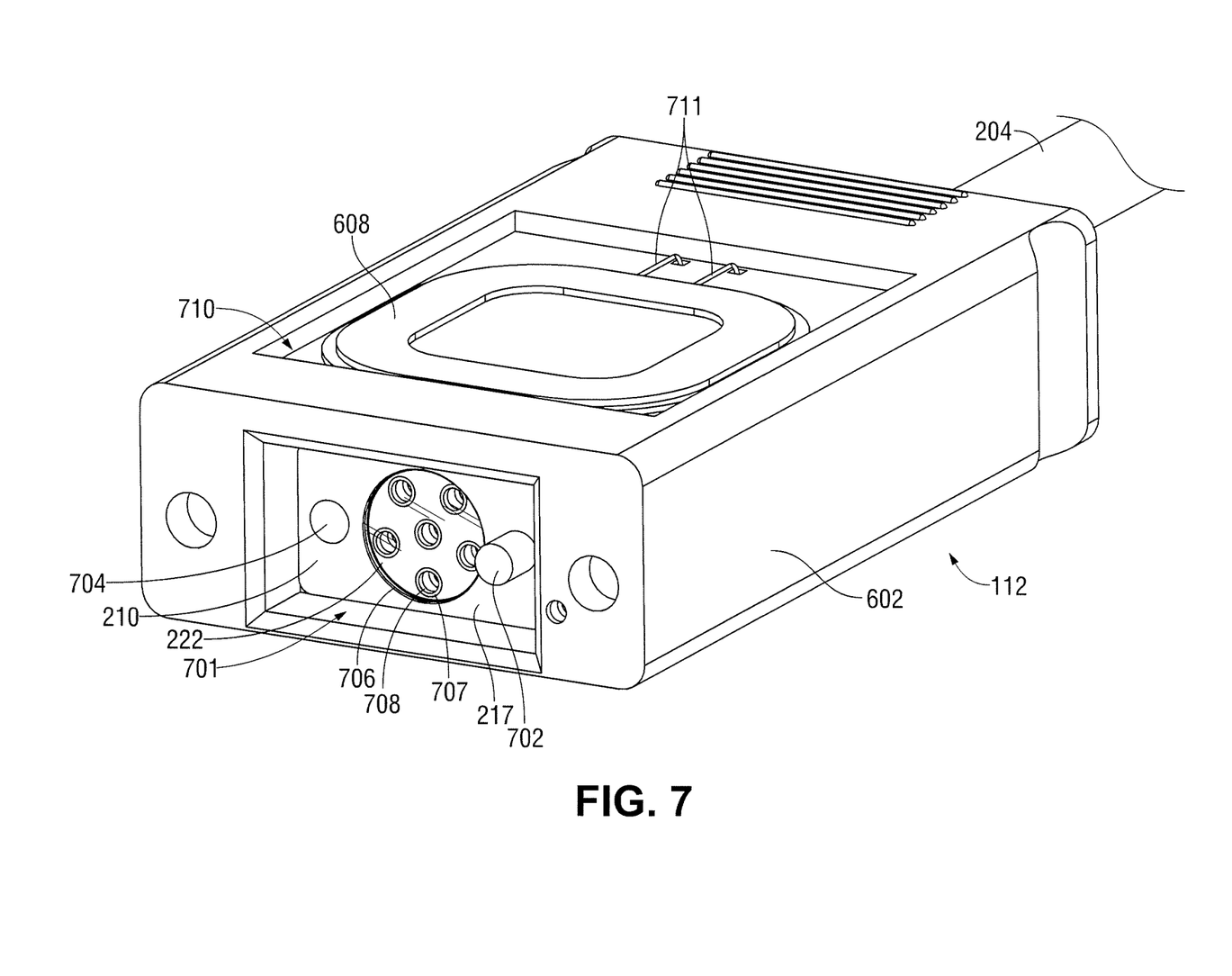
FIG. 7 is a view in perspective showing an end of one of the connectors shown in FIG. 6.

The perspective of FIG. 7 shows an end of connector 112 which is received in receptacle 201 defined by housing 601 in FIG. 6 when the connectors are brought together in the operating position. This end of connector 112 includes a recess 701 in which is mounted the alignment block 217 of connector 112. An alignment pin 702 projects from a face of alignment block 217, while an alignment pin receiver opening 704 is also located on the face of the alignment block. A recess 706 for receiving protective cover 222 is formed between alignment pin 702 and alignment pin receiver 704. An end of the portion of each optical signal path in connector 112 is visible in FIG. 7 within the area of recess 706 behind the transparent protective cover 222. Each such end is defined by a circular opening 707. A lens retainer 708 is apparent in each such circular opening in the perspective of FIG. 7, although components within each optical signal path are not visible in this view. Components within each optical signal path are, however, shown in the section view of FIG. 9, as will be described below.

Figure 8:
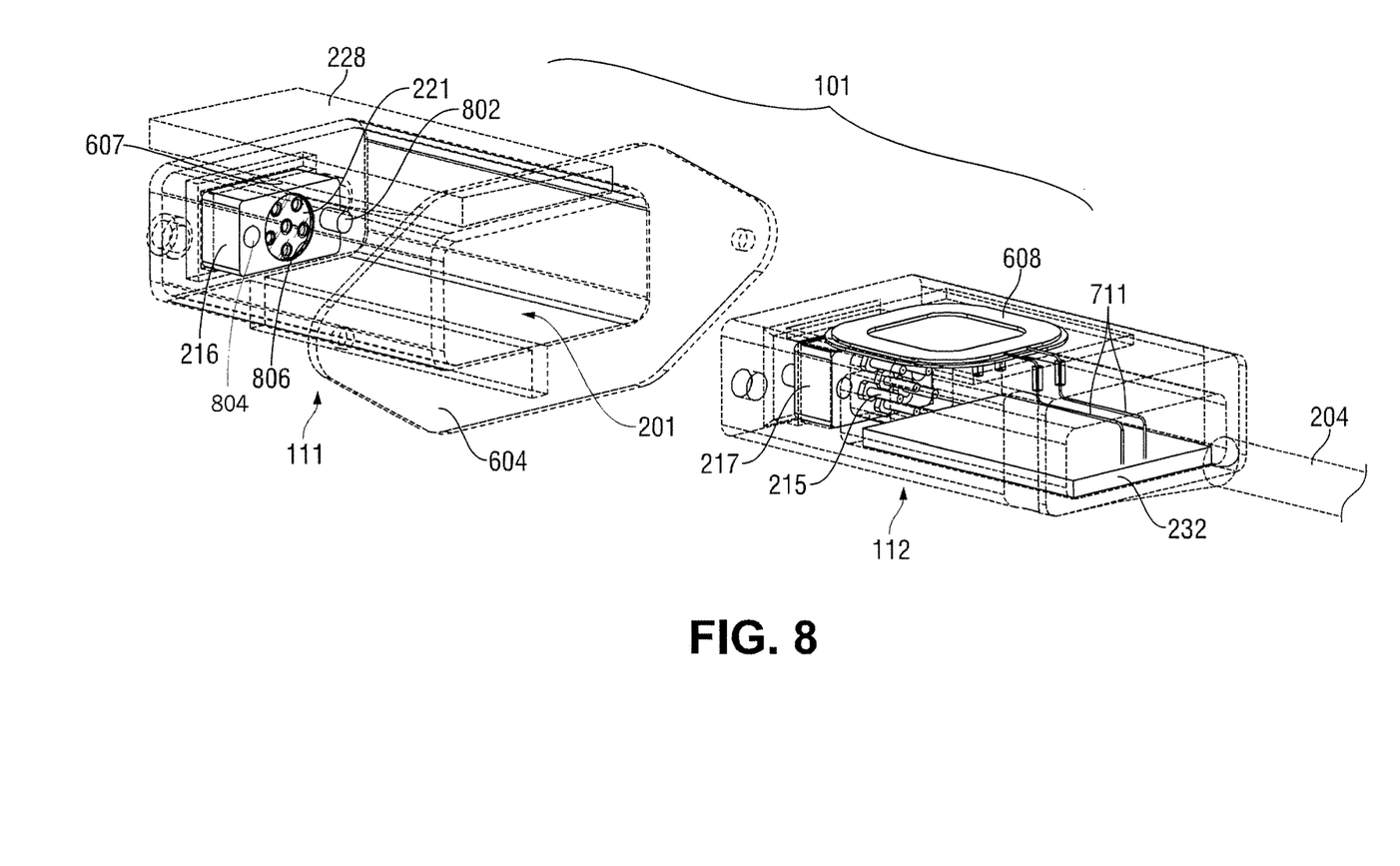
FIG. 8 is a view in perspective similar to FIG. 6, but showing the housing of each connector and certain other features in dashed lines to show the internal components of the connectors and their position relative to the respective housing.

FIG. 8 shows both connectors 111 and 112 aligned so that they may be brought together in the operating position. The connector housings (housing 601 and 602) are shown in dashed lines in FIG. 8 (as are power control circuit 228 and coil 607 for connector 111) so that the internal components of each connector are visible. The internal components of each connector are also shown in the section view of FIG. 9 which is taken along a vertical plane through the center longitudinal axis of the connectors 111 and 112 in the operating position.

Figure 9:
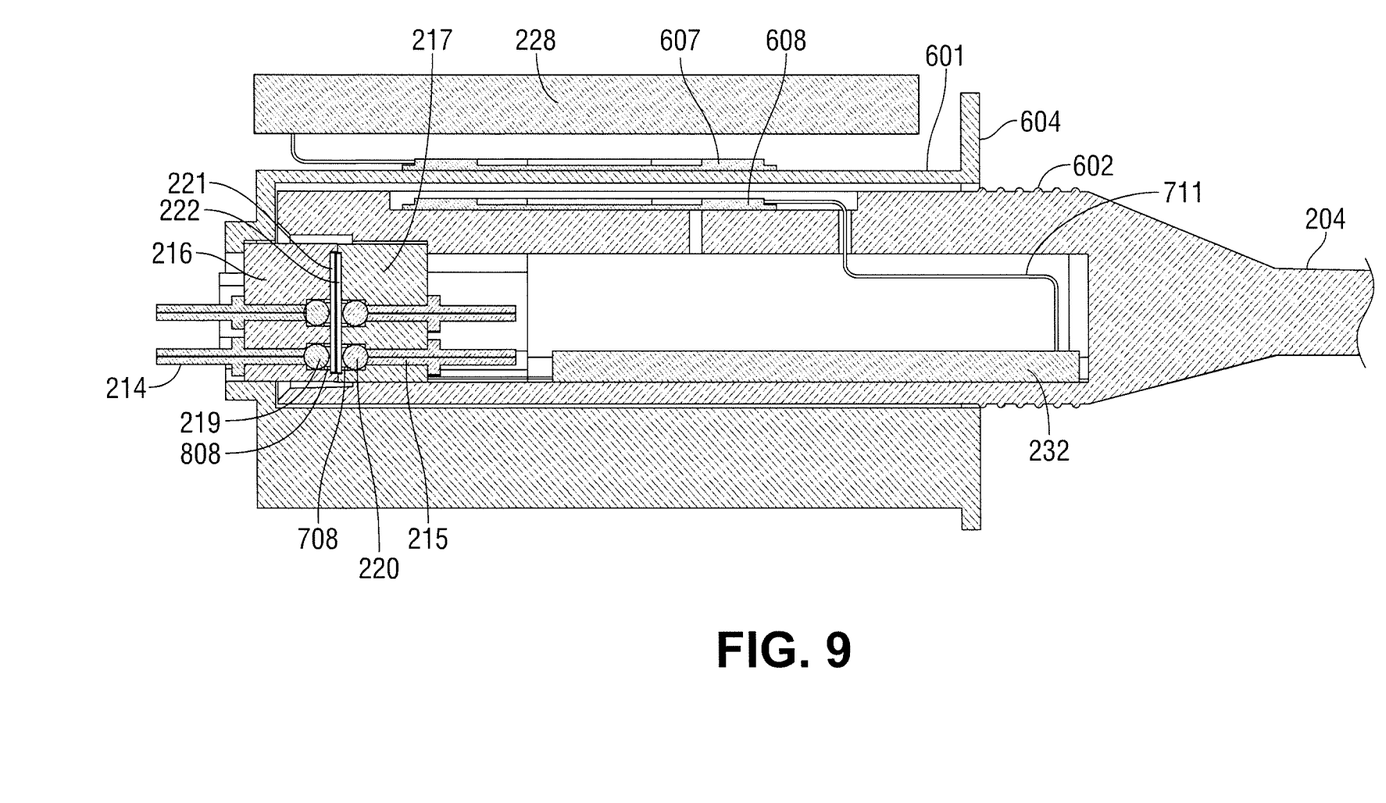
FIG. 9 is a view in section though the connectors shown in FIGS. 6 and 8 in an operating position, the section being taken along a vertical plane through the center longitudinal axis of the connectors.

FIGS. 8 and 9 show alignment block 216 for connector 111 and alignment block 217 for connector 112. As is apparent from FIG. 8, alignment block 216 includes a complementary structure to alignment block 217 with an alignment pin 802 and an alignment pin receiver opening 804. When the two connectors 111 and 112 are brought together in the operating position shown in FIG. 9, the alignment pin of one alignment block is received with close tolerance in the alignment pin receiver opening of the opposite alignment block. This alignment arrangement helps ensure proper alignment of the respective portions of the optical paths formed by the two connectors. As shown in FIG. 8, alignment block 216 also includes a recess 806 in which is mounted transparent protective cover 221. An end of each optical path portion in connector 111 is also visible through the transparent protective material as circular openings although these circular openings are not labeled in the figure in view of the scale of the drawing.

A rear side of alignment block 217 in connector 112 is visible in the view of FIG. 8. This rear side is the side opposite the side shown in the view of FIG. 7. The ferrules 215 for alignment block 217 are visible in FIG. 8, while the section view of FIG. 9 shows two of the ferrules associated with both alignment blocks, namely, ferrules 214 in alignment block 216 and ferrules 215 in alignment block 217. The section view of FIG. 9 also shows the optical lenses 219 and 220, lens retainers 708 and 808, and protective cover material 221 and 222 associated with two of the optical paths defined through the connectors in the operating position.

The example interface device 101 shown in FIGS. 6-9 employs a circular arrangement of ferrules in each alignment block (216, 217). That is, the arrangement includes five ferrules arranged in a circle with the sixth ferrule in the center of that circular shape. The circular arrangement is desirable because it makes efficient use of space in the alignment blocks. However, ferrules may be arranged in any pattern in an alignment block in embodiments of the invention to suit the given application.

It should be noted here that both FIGS. 8 and 9 omit the optical fibers which would be included in connectors 111 and 112 (as shown in FIG. 2) and also omit the electrical conductors extending from circuits 228 and 232. The fibers and conductors are omitted from these views in order to better show the remaining structure of the connectors. Those familiar with optical fiber connections will appreciate that the respective fiber received in a given one of the ferrules 214 or 215 would be positioned so that its end is effectively optically coupled to the respective lens 219 or 220. The fiber may or may not abut the lens depending upon the properties of the lens. In connector 112 each fiber would extend away from its respective ferrule and into cable 204. Each fiber in connector 111 would extend from the respective ferrule to the signal conversion unit associated with that connector (such as conversion unit 114 shown in FIGS. 1 and 2).

The embodiment shown in FIGS. 6-9 includes a power transfer arrangement in which the two connectors 111 and 112 are electrically isolated from each other and power is transferred via an inductive coupling. The inductive coupling in this case is between planar spiral coils. Coil 608 is included on connector 112 and mounted with its plane parallel to a top side of housing 602 in the orientation of the figure. Although it is largely obscured in FIG. 6 by power control circuit 228, connector 111 includes a corresponding spiral coil 607. Coil 607 is mounted outside of receptacle 201 with its plane extending parallel to a top side of the connector in the orientation of the figure. As will be described further below in connection particularly with FIG. 9, these locations of the coils 607 and 608 facilitate the desired inductive coupling when the connectors are in the operating position.

FIG. 7 shows that coil 608 is mounted in a top recess 710 in connector housing 602 so that the coil does not protrude from an uppermost plane of the connector. Conductors 711 extend to the power receiving/conditioning circuit 232 (shown in FIG. 8) inside housing 602. Although this recessed arrangement for coil 608 is preferred, other forms of the invention may use a planar coil that is mounted on top of the top surface of housing 602 so that the coil protrudes somewhat from that surface.

FIG. 9 shows that the two coils are aligned for inductive coupling when the connectors are placed in the operating position. In particular, the position of each coil in its respective connector allows the two coils to reside essentially parallel to each other and in alignment when the connectors are placed in the operating position. This alignment of coils 607 and 608 produces an inductive coupling between the two coils to allow transfer of electrical power from connector 111 to connector 112 as described above.

Regardless of the power transfer arrangement that may be used in a given embodiment of the present invention, and regardless of the number of optical signal paths employed for data communications across interface device 101, connectors 111 and 112 will be held securely together in the operating position in order to form the desired interface. Any suitable technique or combinations of arrangements may be used within the scope of the invention to secure connectors 111 and 112 in the desired operating position to facilitate power transfer and data communication, but allow the connectors to be readily separated as desired. For example, detents may be included on the exterior of one connector and cooperate with corresponding projections on the opposite connector to retain connectors 111 and 112 in the desired operating position. In another arrangement, one connector may include a locking feature such as a suitable ridge and the other connector may include a cooperating latch piece adapted to reside in either a locking position in which it contacts the locking feature to retain the connectors in the operating position, or a release position in which the connectors may be separated. In the example of FIGS. 6-9, the alignment pins 702 and 802 and alignment pin receiving openings 704 and 804 may be formed from suitable material and sized to provide a friction fit which holds the two connectors together once in the operating position until a suitable separating force is applied to separate the connectors.

The various components of an interface according to the present invention may be formed from any suitable material or combination of materials. The materials should be selected for compatibility with environment in which the interface is to be used or to which the interface may be subjected. For example, connectors may be formed from suitable thermoplastics. With regard to cable 204 shown in FIG. 5, cover 501 may comprise reinforced silicone rubber, and EMF shielding may comprise a suitable fine gauge conductive mesh. Filler/reinforcing strands 508 and 515 may be formed from any suitable material which is compatible with the other elements in cable 204 and provides the desired strength characteristics.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An apparatus for providing a detachable data interface to an electrically powered instrument, the apparatus including:
   (a) a first connector;
   (b) a second connector adapted to join with the first connector in an operating position;
   (c) one or more first optical data conduits extending through the first connector, each first optical data conduit terminating at a respective first optical conduit end which is operatively aligned with a respective first optical lens;
   (d) one or more second optical data conduits extending through the second connector, each second optical data conduit terminating at a respective second optical conduit end which is operatively aligned with a respective second optical lens, each respective second optical data conduit and respective second optical lens being aligned for optical coupling across a coupling region with one of the first optical conduits and respective first optical lens when the first connector and second connector are joined in the operating position;
   (e) a first electrical power transfer element mounted on the first connector; and
   (f) a second electrical power transfer element mounted on the second connector, the second electrical power transfer element being located in a power transfer orientation with respect to the first electrical power transfer element when the first connector and second connector are joined in the operating position.

2. The apparatus of claim 1 wherein the first connector defines a receptacle and wherein in the operating position at least a portion of the second connector is received within the receptacle defined by the first connector.

3. The apparatus of claim 2 wherein the first connector is contained within a housing for a camera control unit of an endoscopic system.

4. The apparatus of claim 1 wherein:
   (a) at least a portion of one or more first electrical circuits is included in the first connector;
   (b) at least a portion of one or more second electrical circuits is included in the second connector;
   (c) each first electrical circuit is electrically isolated from each second electrical circuit when the first and second connector are joined in the operating position; and
   (d) the power transfer orientation comprises an orientation facilitating inductive coupling between the first electrical power transfer element and the second electrical power transfer element.

5. The apparatus of claim 1 wherein the first electrical power transfer element comprises a first planar spiral coil and the second electrical power transfer element comprises a second planar spiral coil.

6. The apparatus of claim 5 wherein the first planar spiral coil is aligned parallel to a first side of the first connector and the second planar spiral coil is aligned parallel to a first side of the second connector.

7. The apparatus of claim 1 wherein the first electrical power transfer element comprises a first helical coil and the second electrical power transfer element comprises a second helical coil adapted to align with the first helical coil and reside within an area defined by the first helical coil when the first connector and the second connector are joined in the operating position.

8. The apparatus of claim 1 further including:
(a) a first transparent protective layer mounted on the first connector in position to reside between each first optical lens and the coupling region; and
(b) a second transparent protective layer mounted on the second connector in position to reside between each second optical lens and the coupling region.

9. An apparatus for providing detachable data interface to an electrically powered instrument, the apparatus comprising:
a housing for a camera control unit of an endoscopic system;
a first connector contained within the housing;
at least one first optical data conduit extending through the first connector and terminating at a respective first optical conduit end which is operatively aligned with a respective first optical lens;
a first electrical power transfer element mounted in the first connector;
a second connector adapted to join with the first connector in an operating position;
at least one second optical data conduit extending through the second connector and terminating at a respective second optical conduit end which is operatively aligned with a respective second optical lens; and
a second electrical power transfer element mounted in the second connector,
wherein each respective second optical data conduit and respective second optical lens being aligned for optical coupling across a coupling region with one of the first optical conduits and respective first optical lens when the first connector and second connector are joined in the operating position.

10. The apparatus of claim 9, wherein the second electrical power transfer element being located in a power transfer orientation with respect to the first electrical power transfer element when the first connector and the second connector are joined in the operating position.

11. The apparatus of claim 9, wherein
(a) at least a portion of one or more first electrical circuits is included in the first connector;
(b) at least a portion of one or more second electrical circuits is included in the second connector;
(c) each first electrical circuit is electrically isolated from each second electrical circuit when the first and second connector are joined in the operating position; and
(d) the power transfer orientation comprises an orientation facilitating inductive coupling between the first electrical power transfer element and the second electrical power transfer element.

12. The apparatus of claim 9, wherein the first electrical power transfer element comprises a first planar spiral coil and the second electrical power transfer element comprises a second planar spiral coil.

13. The apparatus of claim 9, wherein the first electrical power transfer element comprises a first helical coil and the second electrical power transfer element comprises a second helical coil adapted to align with the first helical coil and reside within an area defined by the first helical coil when the first connector and the second connector are joined in the operating position.

14. The apparatus of claim 9, further comprising:
(a) a first transparent protective layer mounted on the first connector in position to reside between each first optical lens and the coupling region; and
(b) a second transparent protective layer mounted on the second connector in position to reside between each second optical lens and the coupling region.

* * * * *